(12) United States Patent
Rajagopalan et al.

(10) Patent No.: US 10,646,862 B2
(45) Date of Patent: May 12, 2020

(54) UPGRADING FUEL GAS USING STOICHIOMETRIC AIR FOR CATALYST REGENERATION

(71) Applicant: ExxonMobil Research and Engineering Company, Annandale, NJ (US)

(72) Inventors: Suriyanarayanan Rajagopalan, Spring, TX (US); Mohsen N. Harandi, New Hope, PA (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 10 days.

(21) Appl. No.: 15/825,165

(22) Filed: Nov. 29, 2017

(65) Prior Publication Data

US 2018/0169644 A1 Jun. 21, 2018

Related U.S. Application Data

(60) Provisional application No. 62/434,445, filed on Dec. 15, 2016.

(51) Int. Cl.
| | | |
|---|---|---|
| *B01J 38/12* | (2006.01) | |
| *B01J 29/90* | (2006.01) | |
| *B01J 38/30* | (2006.01) | |
| *B01J 29/44* | (2006.01) | |
| *B01J 29/12* | (2006.01) | |
| *B01J 8/18* | (2006.01) | |
| *B01J 8/26* | (2006.01) | |

(Continued)

(52) U.S. Cl.
CPC .............. *B01J 38/12* (2013.01); *B01J 8/1872* (2013.01); *B01J 8/26* (2013.01); *B01J 29/126* (2013.01); *B01J 29/40* (2013.01); *B01J 29/44* (2013.01); *B01J 29/90* (2013.01); *B01J 38/30* (2013.01); *C07C 2/12* (2013.01); *C10G 50/00* (2013.01); *B01J 2229/42* (2013.01); *C10G 2300/1092* (2013.01); *C10G 2400/02* (2013.01)

(58) Field of Classification Search
CPC . B01J 38/12; B01J 29/126; B01J 29/44; B01J 38/30; B01J 29/90; B01J 29/40; B01J 8/26; B01J 8/1872; B01J 2229/42; C10G 50/00; C10G 2400/02; C10G 2300/1092; C07C 2/12
See application file for complete search history.

(56) References Cited

U.S. PATENT DOCUMENTS

| | | |
|---|---|---|
| 3,354,078 A | 11/1967 | Miale et al. |
| 3,702,886 A | 11/1972 | Argauer et al. |

(Continued)

FOREIGN PATENT DOCUMENTS

| | | |
|---|---|---|
| EP | 0009894 A1 | 4/1980 |
| EP | 0426400 B1 | 3/1995 |

OTHER PUBLICATIONS

Weisz et al., "Superactive Crystalline Aluminosilicate Hydrocarbon Catalysts", Journal of Catalysis, 1965, pp. 527-529, vol. 4.

(Continued)

*Primary Examiner* — Ali Z Fadhel
(74) *Attorney, Agent, or Firm* — Hsin Lin; Chad A. Guice

(57) ABSTRACT

Systems and methods are provided for catalyst regeneration using a stoichiometric amount or less air for coke combustion.

16 Claims, 1 Drawing Sheet

(51) Int. Cl.
  *B01J 29/40* (2006.01)
  *C07C 2/12* (2006.01)
  *C10G 50/00* (2006.01)

(56) References Cited

U.S. PATENT DOCUMENTS

| | | | |
|---|---|---|---|
| 3,709,979 A | 1/1973 | Chu | |
| 3,832,449 A | 8/1974 | Rosinski et al. | |
| 3,948,757 A * | 4/1976 | Strother | B01J 8/26 208/74 |
| 4,016,218 A | 4/1977 | Haag et al. | |
| 4,016,245 A | 4/1977 | Plank et al. | |
| 4,076,842 A | 2/1978 | Plank et al. | |
| 4,104,151 A | 8/1978 | Rubin et al. | |
| 4,417,975 A * | 11/1983 | Myers | B01J 8/1836 208/113 |
| 4,440,632 A | 4/1984 | Vasalos et al. | |
| 4,547,616 A | 10/1985 | Avidan et al. | |
| 4,579,999 A | 4/1986 | Gould et al. | |
| 4,751,338 A | 6/1988 | Tabak et al. | |
| 4,810,357 A | 3/1989 | Chester et al. | |
| 4,827,069 A | 5/1989 | Kushnerick et al. | |
| 4,939,314 A * | 7/1990 | Harandi | B01J 29/90 502/41 |
| 4,954,325 A | 9/1990 | Rubin et al. | |
| 4,965,232 A | 10/1990 | Mauleon et al. | |
| 4,992,607 A * | 2/1991 | Harandi | C07C 2/66 585/322 |
| 5,464,591 A * | 11/1995 | Bartholic | B01J 8/001 208/127 |
| 5,883,031 A * | 3/1999 | Innes | B01J 29/90 208/138 |
| 2004/0064007 A1 * | 4/2004 | Beech | B01J 8/0055 585/639 |
| 2011/0240522 A1 | 10/2011 | Stine | |

OTHER PUBLICATIONS

Miale et al., "Catalysis by Crystalline Aluminosilicates", Journal of Catalysis, 1966, pp. 278-287, vol. 6.

Olson et al., "Chemical and Physical Properties of the ZSM-5 Substituional Series", Journal of Catalysis, 1980, pp. 390-396, vol. 61.

The International Search Report and Written Opinion of PCT/US2017/063576 dated Feb. 28, 2018.

The International Search Report and Written Opinion of PCT/US2017/063552 dated Jan. 24, 2018.

\* cited by examiner

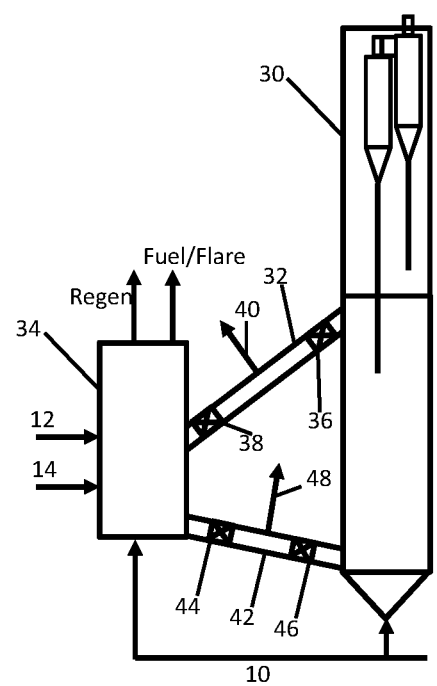

UPGRADING FUEL GAS USING STOICHIOMETRIC AIR FOR CATALYST REGENERATION

CROSS-REFERENCE TO RELATED APPLICATIONS

This application claims priority to U.S. Provisional Application Ser. No. 62/434,445 filed Dec. 15, 2016, which is herein incorporated by reference in its entirety.

This application is related to one other co-pending U.S. application, filed on even date herewith, and identified by the following entitled "Upgrading Hydrocarbons Using Stoichiometric Or Below Stoichiometric Air For Catalyst Regeneration". This co-pending U.S. application is hereby incorporated by reference herein in its entirety.

FIELD

This application relates to the field of fuel gas upgrading using a fluidized bed reactor with an integrated catalyst regenerator.

BACKGROUND

Olefin-containing fuel gas may be upgraded to gasoline using a Mobil Olefins to Gasoline ("MOG") process. In this process, a fluidized bed reactor containing a catalyst, such as ZSM-5, receives the fuel gas feed and oligomerizes olefins in the fuel gas to produce C5+ gasoline. Catalyst particles are circulated to a regenerator to burn the coke that is formed during the oligomerization reactions. Typically, multiple times the stoichiometric air requirement (i.e., a theoretical excess amount of air) is fed to the regenerator to maintain the desired superficial velocity in the regenerator, to achieve a desirable vessel diameter, and to achieve the complete combustion of coke. The reason this is so, is because, the coke make in the MOG process as a wt % of the feed olefins, is less when compared to conventional fluid catalytic cracking units.

SUMMARY

In one aspect, a method is provided for upgrading a fuel gas comprising contacting a fuel gas with a catalyst in a fluidized bed reactor to upgrade the fuel gas to gasoline boiling range hydrocarbons; gravity-feeding a portion of the catalyst from the fluidized bed reactor to a regeneration zone by opening a first pair of block valves on a reactor drain line; closing the first pair of block valves on the reactor drain line and opening a first bleed valve positioned between the first pair of block valves on the reactor drain line; purging the regeneration zone to remove hydrocarbons that are entrained on the portion of the catalyst; exposing the portion of the catalyst to oxygen to regenerate the portion of the catalyst while the portion of the catalyst is in the regeneration zone; purging the regeneration zone to remove oxygen that is entrained in the portion of the catalyst that has been regenerated; pressurizing the regeneration zone with the fuel gas; and feeding the portion of the catalyst that has been regenerated to the fluidized bed reactor by opening a second pair of block valves in a drain line from the regeneration zone.

In another aspect, a system is provided for upgrading a fuel gas comprising: a fluidized bed reactor receiving a fuel gas feed and containing a catalyst suitable for converting the fuel gas to gasoline boiling range hydrocarbons; a regenerator for regenerating the catalyst; a reactor drain line fluidly connected to the fluidized bed reactor and the regenerator having a first end proximal an outlet of the fluidized bed reactor and a second end proximal an inlet of the regenerator, wherein the first end is higher than the second end; a first pair of block valves on the reactor drain line; a first bleed valve on the reactor drain line between the first pair of block valves; a regenerator drain line fluidly connected to the regenerator and the fluidized bed reactor having a first end proximal an outlet of the regenerator and a second end proximal an inlet of the fluidized bed reactor, wherein the first end is higher than the second end; and a second pair of block valves on the regenerator drain line.

DRAWINGS

FIG. 1 is a schematic illustrating an exemplary process of regeneration of catalyst according to one or more embodiments of the present invention.

DETAILED DESCRIPTION

Systems and methods are provided for catalyst regeneration using a stoichiometric amount or less air for coke combustion. Such a system and method may allow for reduction in air compressor, start-up heater demands and sizes, reduction in the regenerator size, and the structural demands to accommodate the regenerator.

These and other advantages may be achieved by contacting a fuel gas with a catalyst, such as ZSM-5, in a fluidized bed reactor to upgrade the fuel gas to gasoline boiling range hydrocarbons; gravity-feeding a portion of the catalyst from the fluidized bed reactor to a regeneration zone by opening a first pair of block valves on a reactor drain line; closing the first pair of block valves on the reactor drain line and opening a first bleed valve positioned between the first pair of block valves on the reactor drain line; purging the regeneration zone to remove hydrocarbons that are entrained on the portion of the catalyst; exposing the portion of the catalyst to oxygen to regenerate the portion of the catalyst while the portion of the catalyst is in the regeneration zone; purging the regeneration zone to remove oxygen that is entrained in the portion of the catalyst that has been regenerated; pressurizing the regeneration zone with the fuel gas; and feeding the portion of the catalyst that has been regenerated to the fluidized bed reactor by opening a second pair of block valves in a drain line from the regeneration zone.

In any embodiment, the step of exposing the portion of the catalyst to oxygen can involve directing combustion air into the regeneration zone at a rate of about 100.05% or less, such as about 100% or less, of the stoichiometric air requirement for combusting coke present on the portion of catalyst.

In any embodiment, the method may also include closing the second pair of block valves on the drain line of the regeneration zone and opening a second bleed valve positioned between the second pair of block valves on the drain line of the regeneration zone. The portion of the catalyst that has been regenerated may be fed through the drain line from the regeneration zone by gravity.

Systems are provided for upgrading a fuel gas comprising: a fluidized bed reactor receiving a fuel gas feed and containing a catalyst suitable for converting the fuel gas to gasoline boiling range hydrocarbons; a regenerator for regenerating the catalyst; a reactor drain line fluidly connected to the fluidized bed reactor and the regenerator having a first end proximal an outlet of the fluidized bed reactor and a second end proximal an inlet of the regenerator, wherein the first end is higher than the second end; a first pair of block valves on the reactor drain line; a first bleed valve on the reactor drain line between the first pair of block valves; a regenerator drain line fluidly connected to the regenerator and the fluidized bed reactor having a first end proximal an outlet of the regenerator and a second end proximal an inlet of the fluidized bed reactor, wherein the first end is higher than the second end; and a second pair of block valves on the regenerator drain line.

In any embodiment, a first block valve of the first pair of block valves may be positioned adjacent to the outlet of the fluidized bed reactor. A second block valve of the first pair of block valves may be positioned adjacent to the inlet of the regenerator. In addition, a first block valve of the second pair of block valves may be positioned adjacent to the inlet of the fluidized bed reactor, and a second block valve of the second pair of block valves may be positioned adjacent to the outlet of the regenerator. A second bleed valve may be positioned on the regenerator drain line between the second pair of block valves.

The regenerator may receive a fuel gas feed stream, an oxygen feed stream supplying a gas comprising oxygen to the regenerator, and a nitrogen purge feed stream supplying nitrogen to the regenerator. Multiple effluent streams may also be provided from the regenerator including lines for carrying fuel gas to be used as fuel or flare, off-gas lines for carrying off-gases to useful locations in the refinery (such as tying into off-gases from a fluid catalytic cracking unit). Similarly, the bleed valves can be tied to lines that direct the fuel gas to a flare.

As used herein, and unless specified otherwise, "gasoline" or "gasoline boiling range hydrocarbons" refers to a composition containing at least predominantly C5-C12 hydrocarbons. In one embodiment, gasoline or gasoline boiling range components is further defined to refer to a composition containing at least predominantly C5-C12 hydrocarbons and further having a boiling range of from about 100° F. to about 400° F. In an alternative embodiment, gasoline or gasoline boiling range components is defined to refer to a composition containing at least predominantly C5-C12 hydrocarbons, having a boiling range of from about 100° F. to about 400° F., and further defined to meet ASTM standard D439.

Hydrocarbon Feeds

The present processes and systems may be employed with various hydrocarbon feeds; however, the processes and systems disclosed herein are particularly useful in upgrading fuel gas to gasoline range hydrocarbons. For example, the hydrocarbon feed may be a fuel gas comprising C5-hydrocarbons, particularly fuel gas feedstreams comprising C4 and lighter hydrocarbons, including feedstreams that are predominantly C3 hydrocarbons or feedstreams that comprise C2-hydrocarbons.

The present processes and systems may also be employed with the regeneration of catalysts for desulfurization, such as those used in fluidized reactor beds to remove sulfur from naphtha streams produced by fluid catalytic cracking units.

Reaction System

In various aspects, the hydrocarbon feed can be exposed to an acidic catalyst (such as a zeolite) under effective conversion conditions for olefinic oligomerization and/or sulfur removal. Optionally, the zeolite or other acidic catalyst can also include a hydrogenation functionality, such as a Group VIII metal or other suitable metal that can activate hydrogenation/dehydrogenation reactions. The hydrocarbon feed can be exposed to the acidic catalyst without providing substantial additional hydrogen to the reaction environment. Added hydrogen refers to hydrogen introduced as an input flow to the process, as opposed to any hydrogen that might be generated in-situ during processing. Exposing the feed to an acidic catalyst without providing substantial added hydrogen is defined herein as exposing the feed to the catalyst in the presence of a) less than about 100 SCF/bbl of added hydrogen, or less than about 50 SCF/bbl; b) a partial pressure of less than about 50 psig (350 kPag), or less than about 15 psig (100 kPag) of hydrogen; or c) a combination thereof The acidic catalyst used in the processes described herein can be a zeolite-based catalyst, that is, it can comprise an acidic zeolite in combination with a binder or matrix material such as alumina, silica, or silica-alumina, and optionally further in combination with a hydrogenation metal. More generally, the acidic catalyst can correspond to a molecular sieve (such as a zeolite) in combination with a binder, and optionally a hydrogenation metal. Molecular sieves for use in the catalysts can be medium pore size zeolites, such as those having the framework structure of ZSM-5, ZSM-11, ZSM-12, ZSM-22, ZSM-23, ZSM-35, ZSM-48, or MCM-22. Such molecular sieves can have a 10-member ring as the largest ring size in the framework structure. The medium pore size zeolites are a well-recognized class of zeolites and can be characterized as having a Constraint Index of 1 to 12. Constraint Index is determined as described in U.S. Pat. No. 4,016,218 incorporated herein by reference. Catalysts of this type are described in U.S. Pat. Nos. 4,827,069 and 4,992,067 which are incorporated herein by reference and to which reference is made for further details of such catalysts, zeolites and binder or matrix materials.

Additionally or alternately, catalysts based on large pore size framework structures (12-member rings) such as the synthetic faujasites, especially zeolite Y, such as in the form of zeolite USY. Zeolite beta may also be used as the zeolite component. Other materials of acidic functionality which may be used in the catalyst include the materials identified as MCM-36 and MCM-49. Still other materials can include other types of molecular sieves having suitable framework structures, such as silicoaluminophosphates (SAPOs), aluminosilicates having other heteroatoms in the framework structure, such as Ga, Sn, or Zn, or silicoaluminophosphates having other heteroatoms in the framework structure. Mordenite or other solid acid catalysts can also be used as the catalyst.

In various aspects, the exposure of the hydrocarbon feed to the acidic catalyst can be performed in any convenient manner, such as exposing the hydrocarbon feed to the acidic catalyst under fluidized bed conditions, moving bed conditions, and/or in a riser reactor. In some aspects, the particle size of the catalyst can be selected in accordance with the fluidization regime which is used in the process. Particle size distribution can be important for maintaining turbulent fluid bed conditions as described in U.S. Pat. No. 4,827,069 and incorporated herein by reference. Suitable particle sizes and distributions for operation of dense fluid bed and transport bed reaction zones are described in U.S. Pat. Nos. 4,827,069 and 4,992,607 both incorporated herein by reference. Particle sizes in both cases will normally be in the range of 10 to 300 microns, typically from 20 to 100 microns.

Acidic zeolite catalysts suitable for use as described herein can be those exhibiting high hydrogen transfer activity and having a zeolite structure of ZSM-5, ZSM-11, ZSM-12, ZSM-22, ZSM-23, ZSM-35, ZSM-48, MCM-22, MCM-36, MCM-49, zeolite Y, and zeolite beta. Such catalysts can be capable of oligomerizing olefins from the hydrocarbon feed. For example, such catalysts can convert C2-C4 olefins, such as those present in a refinery fuel gas, to C5+ olefins. Such catalysts can also be capable of converting organic sulfur compounds such as mercaptans to hydrogen sulfide without added hydrogen by utilizing hydrogen present in the hydrocarbon feed. Group VIII metals such as nickel may be used as desulfurization promoters. A fluid-bed reactor/regenerator can assist with maintaining catalyst activity in comparison with a fixed-bed system. Further, the hydrogen sulfide produced in accordance with the processes described herein can be removed using conventional amine based absorption processes.

ZSM-5 crystalline structure is readily recognized by its X-ray diffraction pattern, which is described in U.S. Pat. No. 3,702,866. ZSM-11 is disclosed in U.S. Pat. No. 3,709,979, ZSM-12 is disclosed in U.S. Pat. No. 3,832,449, ZSM-22 is disclosed in U.S. Pat. No. 4,810,357, ZSM-23 is disclosed in U.S. Pat. Nos. 4,076,842 and 4,104,151, ZSM-35 is disclosed in U.S. Pat. No. 4,016,245, ZSM-48 is disclosed in U.S. Pat. No. 4,375,573 and MCM-22 is disclosed in U.S. Pat. No. 4,954,325. The U.S. Patents identified in this paragraph are incorporated herein by reference.

While suitable zeolites having a coordinated metal oxide to silica molar ratio of 20:1 to 200:1 or higher may be used, it can be advantageous to employ aluminosilicate ZSM-5 having a silica:alumina molar ratio of about 25:1 to 70:1, suitably modified. A typical zeolite catalyst component having Bronsted acid sites can comprises, consist essentially of, or consist of crystalline aluminosilicate having the structure of ZSM-5 zeolite with 5 to 95 wt. % silica, clay and/or alumina binder.

These siliceous zeolites can be employed in their acid forms, ion-exchanged or impregnated with one or more suitable metals, such as Ga, Pd, Zn, Ni, Co, Mo, P, and/or other metals of Periodic Groups III to VIII. The zeolite may include other components, generally one or more metals of group IB, IIB, IIIB, VA, VIA or VIIIA of the Periodic Table (IUPAC).

Useful hydrogenation components can include the noble metals of Group VIIIA, such as platinum, but other noble metals, such as palladium, gold, silver, rhenium or rhodium, may also be used. Base metal hydrogenation components may also be used, such as nickel, cobalt, molybdenum, tungsten, copper or zinc.

The catalyst materials may include two or more catalytic components which components may be present in admixture or combined in a unitary multifunctional solid particle.

In addition to the preferred aluminosilicates, the gallosilicate, ferrosilicate and "silicalite" materials may be employed. ZSM-5 zeolites can be useful in the process because of their regenerability, long life and stability under the extreme conditions of operation. Usually the zeolite crystals have a crystal size from about 0.01 to over 2 microns or more, such as 0.02-1 micron.

In various aspects, the catalyst particles can contain about 25 wt. % to about 40 wt. % H-ZSM-5 zeolite, based on total catalyst weight, contained within a silica-alumina matrix. Typical Alpha values for the catalyst can be about 100 or less. Sulfur conversion to hydrogen sulfide can increase as the alpha value increases.

The Alpha Test is described in U.S. Pat. 3,354,078, and in the Journal of Catalysis, Vol. 4, p. 527 (1965); Vol. 6, p. 278 (1966); and Vol. 61, p. 395 (1980), each incorporated herein by reference as to that description.

In various aspects, the hydrocarbon feed may be exposed to the acidic catalyst by using a moving or fluid catalyst bed reactor. In such aspects, the catalyst may be regenerated, such via continuous oxidative regeneration. The extent of coke loading on the catalyst can then be continuously controlled by varying the severity and/or the frequency of regeneration. In a turbulent fluidized catalyst bed the conversion reactions are conducted in a vertical reactor column by passing hot reactant vapor upwardly through the reaction zone and/or reaction vessel at a velocity greater than dense bed transition velocity and less than transport velocity for the average catalyst particle. A continuous process is operated by withdrawing a portion of coked catalyst from the reaction zone and/or reaction vessel, oxidatively regenerating the withdrawn catalyst and returning regenerated catalyst to the reaction zone at a rate to control catalyst activity and reaction severity to affect feedstock conversion. Preferred fluid bed reactor systems are described in Avidan et al U.S. Pat. No. 4,547,616; Harandi & Owen U.S. Pat. No. 4,751,338; and in Tabak et al U.S. Pat. No. 4,579,999, incorporated herein by reference. In other aspects, other types of reactors can be used, such as fixed bed reactors, riser reactors, fluid bed reactors, and/or moving bed reactors.

In one or more aspects, effective conversion conditions for exposing the hydrocarbon feed to an acidic catalyst can include a temperature of about 300° F. (149° C.) to about 900° F. (482° C.), or about 350° F. (177° C.) to about 850° F. (454° C.), or about 350° F. (177° C.) to about 800° F. (427° C.), or about 350° F. (177° C.) to about 750° F. (399° C.), or about 350° F. (177° C.) to about 700° F. (371° C.), or a temperature of at least about 400° F. (204° C.), or at least about 500° F. (260° C.), or at least about 550° F. (288° C.), or at least about 600° F. (316° C.); a pressure of about 50 psig (0.34 MPag) to about 1100psig (7.6MPag), or a pressure of about 100 psig (0.69 MPag) to about 1000 psig (6.9 MPag), or a pressure of about 100 psig (0.69 MPag) to about 200 psig (1.4 MPag), or about 150 psig (1.0 MPag) to about 975 psig (6.7 MPag), or about 200 psig (1.4 MPag) to about 950 psig (6.6 MPag), or about 250 psig (1.7 MPag) to about 900 psig (6.2 MPag), or about 300 psig (4.1 MPag) to about 850 psig (5.9 MPag), or about 300 psig (4.1 MPag) to about 800 psig (5.5 MPag), or a pressure of at least about 50 psig (0.34 MPag), or a pressure of at least about 100 psig (0.69 MPag), or a pressure of at least about 150 psig (1.0 MPag), or a pressure of at least about 200 psig (1.4 MPag), or a pressure of at least about 250 psig (1.7 MPag), or a pressure of at least about 300 psig (4.1 MPag), or a pressure of at least about 350 psig (2.4 MPag); and a total feed WHSV of about 0.05 hr−1 to about 40 hr−1, or about 0.05 to about 30 hr−1, or about 0.1 to about 20 hr−1, or about 0.1 to about 10 hr−1. Optionally, the total feed WHSV can be about 1 hr−1 to about 40 hr−1 to improve C5+ yield.

In addition to a total feed WHSV, a WHSV can also be specified for just the olefin compounds in the feed. In other words, an olefin WHSV represents a space velocity defined by just the weight of olefins in a feed relative to the weight of catalyst. In one or more aspects, the effective conversion conditions can include an olefin WHSV of at least about 0.3 hr−1, 0.8 hr−1, or at least about 1.0 hr−1, or at least about 2.0 hr−1, or at least about 3.0 hr−1, or at least about 4.0 hr−1, or at least about 5.0 hr−1, or at least about 8.0 hr−1, or at least about 10 hr−1, or at least about 15 hr−1. In the same or alternative aspects, the effective conversion conditions can include an olefin WHSV of about 40 hr−1 or less, or about 30 hr−1 or less, or about 20 hr−1 or less. In certain aspects, the effective conversion conditions can include an olefin WHSV of about 0.3 hr−1 t to about 0.3 hr−1, or about 0.8 hr−1 to about 30 hr−1, or about 0.8 hr−1 to about 20 hr−1, or about 0.8 hr−1 to about 15 hr−1, or about 0.8 hr−1 to about 10 hr−1, or about 0.8 hr−1 to about 7 hr−1, or about 0.8 hr−1 to about 5 hr−1, or about 1.0 hr−1 to about 30 hr−1, or about 1.0 hr−1 to about 20 hr−1, or about 1.0 hr−1 to about 15 hr−1, or about 1.0 hr−1 to about 10 hr−1, or about 1.0 hr−1 to about 7 hr−1, or about 1.0 hr−1 to about 5 hr−1, or about 2.0 hr−1 to about 30 hr−1, or about 2.0 hr−1 to about 20 hr−1, or about 2.0 hr−1 to about 15 hr−1, or about 2.0 hr−1 to about 10 hr−1, or about 2.0 hr−1 to about 7 hr−1, or about 2.0 hr−1 to about 5 hr−1, about 4.0 hr−1 to about 30 hr−1, or about 4.0 hr−1 to about 20 hr−1, or about 4.0 hr−1 to about 15 hr−1, or about 4.0 hr−1 to about 10 hr−1, or about 4.0 hr−1 to about 7 hr−1. An olefin WHSV of about 1 hr−1 to about 40 hr−1 can be beneficial for increasing the C5+ yield.

In various aspects, decreasing the temperature when the olefin WHSV is increased, e.g., when the olefin WHSV is increased above 1 hr−1, may improve product yield. For example, in such aspects, temperatures of about 600° F. (316° C.) to about 800° F. (427° C.), or about 650° F. (343° C.) to about 750° F. (399° C.) may aid in increasing product yield, such as the yield of C5+ compounds, when the olefin WHSV is increased above 1 hr−1.

Regeneration

The catalyst is regenerated to burn coke that is formed and deposited on the catalyst during oligomerization reactions. In embodiments, air may be supplied to the regenerator in about stoichiometric or less than stoichiometric amounts to produce carbon dioxide and carbon monoixide. For example, the regeneration may be conducted with less than 0.05% stoichiometric excess oxygen, inclusive of a stoichiometric oxygen defict.

As illustrated in FIG. 1, the reactor 30, which is a fluidized bed reactor for converting a fuel gas 10 to gasoline boiling range hydrocarbons, includes a reactor drain line 32 for carrying catalyst particles for regeneration to regenerator 34, including double block valves 36, 38 and a bleed valve 40. Although not clearly visible of the schematic of FIG. 1, block valve 36 is positioned on reactor drain line 32 adjacent an outlet of the reactor 30 and block valve 38 is positioned on the reactor drain line 32 adjacent an inlet to the regenerator 34. Bleed valve 40 is positioned on the reactor drain line 32 between block valves 36 and 38. The reactor 30 also includes a regenerator drain line 42 for carrying regenerated catalyst particles back to the reactor 30 including double block valves 44, 46 and a bleed valve 48. Block valve 44 is positioned on the regenerator drain line 42 adjacent an outlet of the regenerator 34 and block valve 46 is positioned on the drain line 42 adjacent an inlet of the reactor 30. Bleed valve 48 is positioned on the regenerator drain line 42 between block valves 44 and 46.

The regenerator 34 includes a fuel gas feed line 10, and feed lines for receiving combustion air 12 and nitrogen 14; The regenerator 34 can include an internal sintered metal filter to aid in the separation of solid catalyst particles from the gases.

Catalyst regeneration may be performed using the following sequence of steps: (1) the double block valves 36, 38 on the reactor drain line 32 are opened with the bleed valve 40 closed and the catalyst particles are drained by gravity into the regenerator 34; (2) once the catalyst particles are transferred to the regenerator 34, the double block valves 36, 38 are closed and the bleed valve 40 is opened; (3) the regenerator 34 which is at a slightly lower pressure than the reactor 30 is depressurized to fuel gas pressure; (4) the regenerator 34 is then purged with nitrogen from nitrogen feed 14 and the entrained fuel gas and nitrogen are sent to be used as fuel or to flare by the opening of one or more valves on a fuel/flare line; (5) the catalyst is regenerated with oxygen via combustion air feed 12 and the off-gas may be routed to tie-in with other refinery off-gas (such as FCC off-gas) or fed to the regenerator 34 itself by the opening of one or more valves on an off gas line (not shown in FIG. 1); (6) oxygen and off-gases are purged from the regenerator 34 with nitrogen, which may continue to be routed to tie in to other refinery off-gas; (7) the regenerator 34 is then pressurized with fuel gas from fuel gas feed 10; (8) the double block valves 42, 46 are opened on the regenerator drain line 42 and the fuel gas fed to regenerator 34 and catalyst contained in regenerator 34 are drained by gravity via regenerator drain line 42 into the reactor 30; and (9) once the regenerated catalyst particles are transferred to the reactor 30, the double block valves 44, 46 are closed and the bleed valve 48 is opened.

Since the reactor 30 has the capability to operate for hours to days without regeneration, regeneration cycles can be managed periodically as needed. Such a configuration reduces the air fed to the regenerator to approximately stoichiometric levels (e.g., less than 0.05% stoichiometric excess oxygen) to produce carbon dioxide and carbon monoxide. Advantageously, such a configuration allows for reduced air compression and air heating, allowing for the physical size, cost and utility demands on such equipment to be reduced. Furthermore, the compressor may be eliminated if a suitable source of air is available.

In such embodiments, the reduced regeneration air requirements allow for reduced air compression and air heating, allowing for the physical size, cost and utility demands on such equipment to be reduced. Furthermore, the compressor may be eliminated if a suitable source of air is available.

Embodiments

In addition to the foregoing, the following embodiments are also considered:

Embodiment 1—A method of upgrading a fuel gas comprising: contacting a fuel gas with a catalyst in a fluidized bed reactor to upgrade the fuel gas to gasoline boiling range hydrocarbons; gravity-feeding a portion of the catalyst from the fluidized bed reactor to a regeneration zone by opening a first pair of block valves on a reactor drain line; closing the first pair of block valves on the reactor drain line and opening a first bleed valve positioned between the first pair of block valves on the reactor drain line; purging the regeneration zone to remove hydrocarbons that are entrained on the portion of the catalyst; exposing the portion of the catalyst to oxygen to regenerate the portion of the catalyst while the portion of the catalyst is in the regeneration zone; purging the regeneration zone to remove oxygen that is entrained in the portion of the catalyst that has been regenerated; pressurizing the regeneration zone with the fuel gas; and feeding the portion of the catalyst that has been regenerated to the fluidized bed reactor by opening a second pair of block valves in a drain line from the regeneration zone.

Embodiment 2—The method of any other enumerated Embodiment, wherein the step of exposing the portion of the catalyst to oxygen comprises directing combustion air into the regeneration zone at a rate of about 100.05% or less of the stoichiometric air requirement for combusting coke present on the portion of catalyst.

Embodiment 3—The method of any other enumerated Embodiment, wherein the catalyst comprises ZSM-5.

Embodiment 4—The method of any other enumerated Embodiment, further comprising closing the second pair of block valves on the drain line of the regeneration zone and opening a second bleed valve positioned between the second pair of block valves on the drain line of the regeneration zone.

Embodiment 5—The method of any other enumerated Embodiment, wherein the portion of the catalyst that has been regenerated is transported through the drain line from the regeneration zone by gravity.

Embodiment 6—The method of any other enumerated Embodiment, wherein a first block valve of the first pair of block valves is positioned adjacent to an outlet of the fluidized bed reactor.

Embodiment 7—The method of any other enumerated Embodiment, wherein a second block valve of the first pair of block valves is positioned adjacent to an inlet of a vessel containing the regeneration zone.

Embodiment 8—A system for upgrading a fuel gas comprising: a fluidized bed reactor receiving a fuel gas feed and containing a catalyst suitable for converting the fuel gas to gasoline boiling range hydrocarbons; a regenerator for regenerating the catalyst; a reactor drain line fluidly connected to the fluidized bed reactor and the regenerator having a first end proximal an outlet of the fluidized bed reactor and a second end proximal an inlet of the regenerator, wherein the first end is higher than the second end; a first pair of block valves on the reactor drain line; a first bleed valve on the reactor drain line between the first pair of block valves; a regenerator drain line fluidly connected to the regenerator and the fluidized bed reactor having a first end proximal an outlet of the regenerator and a second end proximal an inlet of the fluidized bed reactor, wherein the first end is higher than the second end; and a second pair of block valves on the regenerator drain line.

Embodiment 9—The system of any other enumerated Embodiment, wherein a first block valve of the first pair of block valves is positioned adjacent to the outlet of the fluidized bed reactor.

Embodiment 10—The system of any other enumerated Embodiment, wherein a second block valve of the first pair of block valves is positioned adjacent to the inlet of the regenerator.

Embodiment 11—The system of any other enumerated Embodiment, wherein a first block valve of the second pair of block valves is positioned adjacent to the inlet of the fluidized bed reactor.

Embodiment 12—The system of any other enumerated Embodiment, wherein a second block valve of the second pair of block valves is positioned adjacent to the outlet of the regenerator.

Embodiment 13—The system of any other enumerated Embodiment, further comprising a second bleed valve on the regenerator drain line between the second pair of block valves.

Embodiment 14—The system of any other enumerated Embodiment, further comprise a fuel gas feed stream supplying fuel gas to the regenerator.

Embodiment 15—The system of any other enumerated Embodiment, further comprising an oxygen feed stream supplying a gas comprising oxygen to the regenerator.

Embodiment 16—The system of any other enumerated Embodiment, further comprising a nitrogen purge feed stream supplying nitrogen to the regenerator.

The invention claimed is:

1. A method of upgrading a fuel gas comprising:
contacting a fuel gas comprising $C_5$- hydrocarbons with a catalyst in a fluidized bed reactor to upgrade the fuel gas to gasoline boiling range $C_5$—$C_{12}$ hydrocarbons;
gravity-feeding a portion of the catalyst from the fluidized bed reactor to a regeneration zone by opening a first pair of block valves on a reactor drain line;
closing the first pair of block valves on the reactor drain line and opening a first bleed valve positioned between the first pair of block valves on the reactor drain line;
purging the regeneration zone to remove hydrocarbons that are entrained on the portion of the catalyst;
exposing the portion of the catalyst to oxygen to regenerate the portion of the catalyst while the portion of the catalyst is in the regeneration zone;
purging the regeneration zone to remove oxygen that is entrained in the portion of the catalyst that has been regenerated;
pressurizing the regeneration zone with the fuel gas; and
feeding the portion of the catalyst that has been regenerated to the fluidized bed reactor by opening a second pair of block valves in a drain line from the regeneration zone.

2. The method of claim 1, wherein the step of exposing the portion of the catalyst to oxygen comprises directing combustion air into the regeneration zone at a rate of about 100.05% or less of the stoichiometric air requirement for combusting coke present on the portion of catalyst.

3. The method of claim 1, wherein the catalyst comprises ZSM-5.

4. The method of claim 1, further comprising closing the second pair of block valves on the drain line of the regeneration zone and opening a second bleed valve positioned between the second pair of block valves on the drain line of the regeneration zone.

5. The method of claim 1, wherein the portion of the catalyst that has been regenerated is transported through the drain line from the regeneration zone by gravity.

6. The method of claim 1, wherein a first block valve of the first pair of block valves is positioned adjacent to an outlet of the fluidized bed reactor.

7. The method of claim 1, wherein a second block valve of the first pair of block valves is positioned adjacent to an inlet of a vessel containing the regeneration zone.

8. A system for upgrading a fuel gas comprising:
a fluidized bed reactor receiving a fuel gas feed and containing a catalyst suitable for converting the fuel gas to gasoline boiling range hydrocarbons;
a regenerator for regenerating the catalyst;
a reactor drain line fluidly connected to the fluidized bed reactor and the regenerator having a first end proximal an outlet of the fluidized bed reactor and a second end proximal an inlet of the regenerator, wherein the first end is higher than the second end, and wherein the catalyst is drained by gravity from the fluidized bed reactor into the regenerator via the reactor drain line;
a first pair of block valves on the reactor drain line;
a first bleed valve on the reactor drain line between the first pair of block valves;
a regenerator drain line fluidly connected to the regenerator and the fluidized bed reactor having a first end proximal an outlet of the regenerator and a second end proximal an inlet of the fluidized bed reactor, wherein the first end is higher than the second end; and
a second pair of block valves on the regenerator drain line.

9. The system of claim 8, wherein a first block valve of the first pair of block valves is positioned adjacent to the outlet of the fluidized bed reactor.

10. The system of claim 8, wherein a second block valve of the first pair of block valves is positioned adjacent to the inlet of the regenerator.

11. The system of claim 8, wherein a first block valve of the second pair of block valves is positioned adjacent to the inlet of the fluidized bed reactor.

12. The system of claim 8, wherein a second block valve of the second pair of block valves is positioned adjacent to the outlet of the regenerator.

13. The system of claim 8, further comprising a second bleed valve on the regenerator drain line between the second pair of block valves.

14. The system of claim 8, further comprise a fuel gas feed stream supplying fuel gas to the regenerator.

15. The system of claim 8, further comprising an oxygen feed stream supplying a gas comprising oxygen to the regenerator.

16. The system of claim 8, further comprising a nitrogen purge feed stream supplying nitrogen to the regenerator.

\* \* \* \* \*